(12) United States Patent
Barsky

(10) Patent No.: US 7,894,645 B2
(45) Date of Patent: Feb. 22, 2011

(54) HIGH-RESOLUTION DIGITAL IMAGE PROCESSING IN THE ANALYSIS OF PATHOLOGICAL MATERIALS

(75) Inventor: Sanford H. Barsky, Los Angeles, CA (US)

(73) Assignee: Ohio State University, Columbus, OH (US)

( * ) Notice: Subject to any disclaimer, the term of this patent is extended or adjusted under 35 U.S.C. 154(b) by 748 days.

(21) Appl. No.: 10/343,952

(22) PCT Filed: Aug. 9, 2001

(86) PCT No.: PCT/US01/25026

§ 371 (c)(1),
(2), (4) Date: Aug. 1, 2003

(87) PCT Pub. No.: WO02/15559

PCT Pub. Date: Feb. 21, 2002

(65) Prior Publication Data

US 2004/0030232 A1    Feb. 12, 2004

Related U.S. Application Data

(60) Provisional application No. 60/224,252, filed on Aug. 10, 2000.

(51) Int. Cl.
*G06K 9/00* (2006.01)

(52) U.S. Cl. .................. 382/128; 382/218; 707/941

(58) Field of Classification Search ............... 706/924; 382/159, 209, 218, 128, 156, 181, 206; 707/941
See application file for complete search history.

(56) References Cited

U.S. PATENT DOCUMENTS

| | | | |
|---|---|---|---|
| 3,705,383 A * | 12/1972 | Frayer | 382/134 |
| 4,769,850 A | 9/1988 | Itoh et al. | |
| 4,907,156 A | 3/1990 | Doi et al. | |
| 4,945,476 A * | 7/1990 | Bodick et al. | 600/301 |
| 5,072,382 A * | 12/1991 | Kamentsky | 382/133 |
| 5,073,857 A | 12/1991 | Peters et al. | |
| 5,133,020 A | 7/1992 | Giger et al. | |
| 5,220,360 A | 6/1993 | Verdooner et al. | |
| 5,235,510 A | 8/1993 | Yamada et al. | |
| 5,291,560 A | 3/1994 | Daugman et al. | |
| 5,331,550 A | 7/1994 | Stafford et al. | |
| 5,586,160 A | 12/1996 | Mascio | |
| 5,592,374 A | 1/1997 | Fellegara et al. | |
| 5,596,994 A | 1/1997 | Bro | |
| 5,619,995 A | 4/1997 | Lobodzinski | |
| 5,740,270 A | 4/1998 | Rutenberg et al. | |
| 5,761,334 A | 6/1998 | Nakajima et al. | |
| 5,768,333 A | 6/1998 | Abdel-Mottaleb | |
| 5,769,074 A | 6/1998 | Barnhill et al. | |
| 5,787,188 A | 7/1998 | Nelson et al. | |
| 5,793,969 A * | 8/1998 | Kamentsky et al. | 709/213 |
| 5,797,130 A | 8/1998 | Nelson et al. | |
| 5,828,776 A | 10/1998 | Lee et al. | |
| 5,865,745 A | 2/1999 | Schmitt et al. | |
| 5,868,669 A | 2/1999 | Iliff | |
| 5,876,926 A | 3/1999 | Beecham | |
| 5,878,746 A * | 3/1999 | Lemelson et al. | 600/407 |
| 5,933,519 A | 8/1999 | Lee et al. | |
| 5,939,278 A | 8/1999 | Boon et al. | |
| 5,940,535 A | 8/1999 | Huang | |
| 5,960,435 A | 9/1999 | Rathmann et al. | |
| 5,978,497 A | 11/1999 | Lee et al. | |
| 5,980,096 A | 11/1999 | Thalhammer-Reyero | |
| 5,982,917 A | 11/1999 | Clarke et al. | |
| 5,987,094 A | 11/1999 | Clarke et al. | |
| 5,987,158 A | 11/1999 | Meyer et al. | |
| 6,014,451 A * | 1/2000 | Berry et al. | 382/110 |
| 6,014,452 A | 1/2000 | Zhang et al. | |
| 6,021,220 A | 2/2000 | Anderholm | |
| 6,031,929 A | 2/2000 | Maitz et al. | |
| 6,033,076 A | 3/2000 | Braeuning et al. | |
| 6,075,879 A | 6/2000 | Roehrig et al. | |
| 6,081,612 A | 6/2000 | Gutkowicz-Krusin et al. | |
| 6,095,989 A | 8/2000 | Hay et al. | |
| 6,134,354 A | 10/2000 | Lee et al. | |

(Continued)

FOREIGN PATENT DOCUMENTS

WO    WO 91/14202    9/1991

(Continued)

OTHER PUBLICATIONS

Brugal, Pattern Recognition, Image Processing, Related Data Analysis and Expert Systems Integrated in Medical Microscopy, Nov. 14-17, 1988, 9th International Conference on Pattern Recognition, 1998, vol. 1, pp. 286-293.*

Benjamins et al., Artificial Intelligence Approaches for Cytological Image Interpretation, Oct. 2-5, 1994, 1994 IEEE International Conference on Systems, Man, and Cybernetics, vol. 3, pp. 2306-2310.*

Rashbass, The imapact of information technology on histopathology, 2000, Histopathology, pp. 1-7.*

Cross, Clinical Applications of Artificial Neural Networks: Chapter 2: Artificial Neural Networks in Laboratory Medicine, 2001, Cambridge University Press, pp. 31-80.*

(Continued)

*Primary Examiner*—Brian P Werner
*Assistant Examiner*—Dennis Rosario
(74) *Attorney, Agent, or Firm*—MacMillan, Sobanski & Todd, LLC

(57) ABSTRACT

A method and system of ascertaining diagnostic information concerning a pathological specimen over a network is disclosed. The method comprises transmitting a digitized image of a pathological specimen to central location, and then receiving diagnostic information from the central location concerning the pathological specimen after an analysis of the digitized image has been performed at the central location.

7 Claims, No Drawings

U.S. PATENT DOCUMENTS

| | | | |
|---|---|---|---|
| 6,252,979 B1 | 6/2001 | Lee et al. | |
| 6,292,577 B1 * | 9/2001 | Takahashi | 382/128 |
| 6,385,474 B1 * | 5/2002 | Rather et al. | 600/407 |
| 6,611,630 B1 * | 8/2003 | Miller et al. | 382/293 |
| 6,798,914 B1 * | 9/2004 | Nanni et al. | 382/232 |
| 2002/0021828 A1 * | 2/2002 | Papier et al. | 382/128 |
| 2004/0014165 A1 * | 1/2004 | Keidar et al. | 435/40.5 |

FOREIGN PATENT DOCUMENTS

| | | |
|---|---|---|
| WO | WO 96/09604 | 3/1996 |
| WO | WO 96/17545 | 6/1996 |
| WO | WO 97/25678 | 7/1997 |
| WO | WO 99/08091 | 2/1999 |
| WO | WO 00/00079 | 1/2000 |
| WO | WO 00/14668 | 3/2000 |
| WO | WO 00/36524 | 6/2000 |

OTHER PUBLICATIONS

Porto et al, Clinical Applications of Artificial Neural Networs, Chapter 10: Evolving Artificial Neural Netwroks, 2001, Cambridge University Press, pp. 223-234.*

Gibson et al., Definition and Application of a Fourier Domain Texture Measure: Applications to Histological Image Segmentation, 1995, Elsevier Science Ltd: Comput. Biol. Med., vol. 25, No. 6, pp. 551-557.*

* cited by examiner

HIGH-RESOLUTION DIGITAL IMAGE PROCESSING IN THE ANALYSIS OF PATHOLOGICAL MATERIALS

CROSS-REFERENCES AND RELATED APPLICATIONS

This application claims priority to Intl. Pat. App. No. PCT/US01/25026, filed Aug. 9, 2001, which claims priority to U.S. Provisional Pat. App. No. 60/224,252, filed Aug. 10, 2000, both of which are incorporated by reference herein for all purposes.

BACKGROUND OF THE INVENTION

Field of the Invention

The present invention relates to high-resolution image recognition in the microscopical analysis of pathological materials. The invention further relates to systems and methods for transmitting microscopical images over a network for diagnostic and other purposes.

DETAILED DESCRIPTION OF A PREFERRED EMBODIMENT

Imaging Insight ("the Company") plans to use a streamlined product pricing structure and delivery model, and to offer two levels of service. Each will be targeted at two different groups of end-users. Both products will be focused on accessing the Company's proprietary database and the information it contains through a dedicated, high-speed Internet connection.

The first level of service (level I) will be offered to working hospitals, pharmaceutical companies, and others that must ensure a high level of accuracy when identifying pathology samples. This service will allow the user to submit specimens that have been converted to a digital format, engage our search engine, which will compare the submission to all samples in the database, and return a positive match. Our system will permit both computer-assisted diagnosis and computer-independent diagnosis on the basis of digital comparisons of unknown images with the company reference library of digital images.

At the user's location, a specialized Personal Computer (PC) resides on the desktop. A digital microscope resides alongside the PC that will allow the user to convert the specimen to a digital image. Both the PC and the digital microscope can be leased from the Company to the end user, which will allow us to maintain the integrity of the data coming into the system for analysis.

After the specimen has been submitted, the user will also be able to run a report characterizing the matched sample. This report can detail the specific characteristics of the sample, like who is likely to be afflicted with the pathogen in question, their age, race, gender, etc. Further, this report may outline the etiology of the sample, what kind of cancer, how aggressive is the disease, and importantly which treatments may be employed to cure the affliction. End-users will have the ability to "search and query" the database based on text characteristics specified by the user. This first level of service will be the most desirable because of the ability to submit a digital image and have a positive match returned.

Our product will be extremely beneficial to the medical community and will take much of the guesswork out of diagnosing certain cancers and other pathogens that otherwise may be misdiagnosed. Accuracy and integrity of our data will foster an extremely high confidence level among practitioners and will allow all users to "harness processing power" in their diagnosis.

The level II product will be targeted at universities and teaching hospitals, where students, interns, or professors will be able to access our database. Users in this environment will be able to run simple to complex searches of our system based on a wide range of user-specified fields. This may include morphological features, i.e., size of nuclei, degree of blood vessel formation, etc. Level II service will be nearly identical to level I service with one main exception: Level II service will not have the ability to submit digitized specimens and have a positive match returned. The rationale behind this is that universities are not interested in the service as a diagnostic tool but as learning and teaching tool. We envision our products becoming a powerful learning tool for students. If a student wants to learn about a specific cancer, whom it is likely to affect, and related mortality rates, this information will be just a simple query away.

Level II users can have the same PC that level I users have. Both levels of service can have the same advanced search and querying abilities.

All images in our database will be tagged with certain characteristics that can be called qualitative characteristics. These characteristics may include the general appearance of the sample under the microscope, who is likely to contract the disease, what are the statistical characteristics of who is affected, etc. Current technology will allow researchers and students to perform very advanced studies of different diseases and whom they affect and ultimately how they may be treated.

Another site feature allows the user to "drill down" on a specific topic. The Company has a tool whereby results to a user's query not only shows matches to the query and its related characteristics, but shows related links to other web sites with information related to the user's request. For example, if a customer submits a sample of a melanoma and the system returns a match of malignant melanoma, users can access a list of websites with subject-related information. Links to accredited sites can be displayed (e.g., American Cancer Institute, Journal of American Medicine). We can employ filtering software to ensure that customers can only access approved websites through our portal.

Imaging Insight is building its reference database of digital images, first pertaining to pathology, and then branching out to biology and almost every aspect of the medical field that relies on data interpreted in a visual medium. The first pathological images being cataloged include all of the cancer slides residing in the UCLA medical library. Images are saved in a standardized, extremely high-resolution imaging format. After thorough evaluation of different imaging formats has been completed, the lead IT implementation team determines the specific format to be employed.

Once the slide is digitized, it is categorized and placed into the Imaging Insight data farm. Only Imaging Insight and its agents will be allowed to manipulate the database, ensuring its integrity. Server technology is state-of-the-art, allowing high-speed customer access to the system from any remote location. Preliminary study suggests the company will use SUN Microsystems Solaris Servers, which can be provided by, for example, Paracel.

The Company's database can be accessible from a secure link over high-speed lines (either DSL or fractional TI), via a router, to our customers. From the customer's onsite interface they can research, compare, and access any data residing on our servers. Front end access will be provided through a custom-designed graphical user interface (GUI). The interface is preferably Windows-based, point-and-click driven, simple, and easy to use, and will work and appear similar to an Internet Web browser. Management has preliminarily selected Andersen Consulting (AC) to build this interface and the website it will run on. AC will act as the company's main technology integrator to oversee the implementation of all Information Technology based systems.

Imaging Insight will provide a leased computer and digital microscope/camera as a package to each licensed end user. The company's goal is to provide its service to customers in a similar manner to Bloomberg, a company that has been very successful in providing dedicated data feeds to its customers. The customer will have a secure data connection that will have authentication software residing on the client-side that will ensure a secure connection. After a customer enters a service agreement, a technician will respond to the customer's location and perform the final installation of the PC and related equipment, making the final connection between the customer and the company's database. This process will help ensure the integrity of our product and assure there will be no piracy of our services.

Customers that subscribe to level I service will have the ability to submit specimens to the database, which will return a positive match. The method for comparing a submitted sample to the company database will be based on the same technology used by other bio-identity matching systems. Great strides have been made in the biocomputing industry in the past few years. Management has researched companies that provide hardware and software to companies in the bio-computing industry. Management has preliminarily found Paracel, a company headquartered in Pasadena, Calif., which can provide Imaging Insight with the most advanced hardware and software currently available.

Methods of processing and analysis of the digitized images can be performed using existing technology, as will be apparent to those of skill in the art. Such methods can include or otherwise incorporate all or part of the disclosure of image-pattern-recognition and database-comparison programs from any or all of the following U.S. patents, which are hereby incorporated in their entirety by reference: U.S. Pat. No. 5,331,550 to Stafford et al., issued Jul. 19, 1994; U.S. Pat. No. 5,586,160 to Mascio, issued Dec. 17, 1996; U.S. Pat. No. 5,761,334 to Nakajima et al., issued Jun. 2, 1998; U.S. Pat. No. 4,907,156 to Doi et al., issued Mar. 6, 1990; U.S. Pat. No. 4,769,850 to Itoh et al., issued Sep. 6, 1998; U.S. Pat. No. 5,980,096 to Thalhammer-Reyero, issued Nov. 9, 1999; Patent No. 5,133,020 to Giger et al., issued Jul. 21, 1992; U.S. Pat. No. 5,291,560 to Daugman et al., issued Mar. 1, 1994; and U.S. Pat. No. 6,014,452 to Zhang et al., issued Jan. 11, 2000;

With the continued improvement of worldwide data services, Imaging Insight can provide digital medical data to virtually anyone in the world. It is our intent to modernize the medical field and provide a valuable resource to doctors, students, researchers, and medical professionals worldwide.

A system and method involving artificial intelligence-driven recognition based on high resolution digital image analysis has been developed which permits archiving, storage, and identification of anatomical and pathological images (gross, microscopic, and immunocytochemical). This system and method of high-resolution digital image analysis allows for the creation of a library of pathological images which serves as a reference data base for assisted diagnosis, teaching, education, and research. The library of pathological images is all-inclusive, consisting of every anatomical disease process, and all of its protean manifestations, known to man. The library of pathological images is assigned addresses which can readily be retrieved and archived.

Our system of high-resolution digital image analysis allows for artificial intelligence-driven image recognition different from existing technologies but by way of principle, analogous to voice-recognition, retinal-recognition and fingerprint-recognition technologies. Our system permits both computer-assisted diagnosis and computer-independent diagnosis on the basis of digital comparisons of unknown images with the library of pathological images existing in memory. Our system of pathological image recognition and diagnosis is useful as a diagnostic, educational, teaching, and research resource. The latter claim derives from the ability to further analyze the stored images for whatever morphological feature is desired, e.g., size of nuclei, degree of blood vessel formation, etc. This system of image recognition involves proprietary methods of image storage, retrieval, and analysis. The commercial aspects of this invention are myriad and therefore it is our wish to form a company based on this invention and technology, called Imaging Insight, Inc.

We intend to use a Natural Language Retrieval System to retrieve, categorize, and locate histopathological slides and their paraffin blocks, from which we will produce standard and uniform histopathological sections and staining. We will proceed, organ system by organ system, retrieving and categorizing every pathological disease process known to man and all of their histopathological nuances and variations. We will produce images of each histological section. We envision entering at least 10-100 examples of each disease process in our database. In every organ system we estimate that there are between 100-1,000 separate disease processes. So what we are talking about is a large scale: 1,000-100,000 data entry for each organ system. There are approximately 20 different organ systems in the human body. Each image entered will be categorized and identified. For example, if we wanted 100 examples of a benign process of the breast called sclerosing adenosis, we will index these and retrieve them instantaneously. The data entered can be used as a visual database of cases, a database of histopathological comparisons or a database from which digital image analyses could be performed to render diagnoses on unknown slides or their images produced. For this work, we use state-of-the-art equipment, including a microscope (or two) with attached video camera (e.g., laser capture microscope).

What is claimed is:

1. A method of ascertaining diagnostic information concerning a pathological specimen over a network, comprising:
   a) providing a microscopical, histopathological specimen of a first tissue from a patient;
   b) transmitting over a network a first digitized image of the histopathological specimen of the first tissue to a central location comprising an external database of known digitized information generated from images of pathological and normal specimens;
   c) receiving diagnostic information over the network from the central location concerning the histopathological specimen,
   d) comparing the first digitized image to the external database of known digitized information to ascertain diagnostic information about the first digitized image;
   1) the diagnostic information of step c) being determined from a digital computer analysis performed by an image pattern recognition software program, using artificial intelligence, wherein the artificial intelligence comprises driven image recognition, and wherein the image pattern recognition software program compares the first digitized image of the histopathological specimen of step b) to the database of the known digitized information generated from images of pathological and normal specimens, 2) the digital computer analysis of step d1) comprising i) a digital assessment comparing a morphological feature of the histopathological specimen of the first tissue to the database of the known digitized information generated from images of pathological and normal specimens; and ii) outputting a result of the comparison of step i);

wherein the outputted result of step d2ii) comprises the diagnostic information; and wherein the diagnostic information received in step c) and determined in steps d1) and d2) is based on a match between the first digitized image of step b) and at least one known digitized image of a second tissue found in the database of known digitized information generated from images of pathological and normal specimens, of someone other than the patient, the second tissue being of a similar type to the first tissue, the diagnostic information selected from the group consisting of a diagnosis, a grade of cellular abnormality, a diagnostic classification, and epidemiological data related to a pathology of the non-cytological pathological specimen; the related epidemiological data being selected from the group consisting of known disease risk factors, age information, race information, gender information, and probabilistic information; and e) ascertaining a computer determined diagnosis concerning the pathological specimen, the diagnosis being generated by the image pattern recognition software program and being based on the computer analysis of the diagnostic information generated in steps d1) and d2) over the network.

2. The method of claim 1, wherein the pathological specimen comprises a microscopical slide preparation.

3. The method of claim 2, wherein the microscopical slide preparation comprises an immunohistochemical preparation.

4. The method of claim 1, further comprising receiving a treatment recommendation over the network based on the diagnostic information.

5. The method of claim 1, wherein the morphological feature comprises a size of a nucleus or a degree of blood vessel formation.

6. The method of claim 1, wherein diagnosis is generated on the basis of digital comparisons of the first digitized image with the database of known digitized images without the need for a pathologist to make a visual examination or to provide any data input.

7. A method of ascertaining diagnostic information concerning a pathological specimen over a network, comprising:

a) providing a microscopical, histopathological specimen of a first tissue from a patient;

b) transmitting a first digitized image of the histopathological specimen of the first tissue to a central location over a network to an external database of known digitized information generated from images of pathological and normal specimens;

c) receiving diagnostic information over the network from the central location concerning the histopathological specimen, d) comparing the first digitized image to the database of known digitized information generated from images to ascertain diagnostic information about the first digitized image;

1) the diagnostic information of step c) being determined from a digital computer analysis performed by an image pattern recognition software program, using artificial intelligence, wherein the artificial intelligence comprises driven image recognition, and wherein the image pattern recognition software program compares the first digitized image of the histopathological specimen of step b) to the database of the known digitized information generated from images of pathological and normal specimens, 2) the digital computer analysis of step d1) comprising i) a digital assessment comparing a morphological feature of the histopathological specimen of the first tissue to the database of the known digitized information generated from images of pathological and normal specimens;

and ii) outputting a result of the comparison of step i);

wherein the outputted result of step d2ii) comprises the diagnostic information; and wherein the diagnostic information received in step c) and determined in steps d1) and d2) is based on a match between the first digitized image of step b) and at least one known digitized image of a second tissue found in the database of known digitized images of pathological and normal specimens, of someone other than the patient, the second tissue being of a similar type to the first tissue, the diagnostic information selected from the group consisting of a diagnosis, a grade of cellular abnormality, a diagnostic classification, and epidemiological data related to a pathology of the non-cytological pathological specimen; the related epidemiological data being selected from the group consisting of known disease risk factors, age information, race information, gender information, and probabilistic information;

e) providing a diagnosis based on the computer analysis of the diagnostic information generated in steps d1) and d2) over the network; and f) adding the diagnostic information generated in steps d1) and d2) to the external database of known digitized images of pathological and normal specimens as a new known digitized image.

* * * * *